United States Patent [19] [11] 4,083,963
Celmer et al. [45] Apr. 11, 1978

[54] POLYPEPTIDE ANTIBIOTIC PRODUCED BY A NEW SUBSPECIES OF STREPTOSPORANGIUM

[75] Inventors: Walter D. Celmer, New London; Walter P. Cullen, East Lyme; Charles E. Moppett, Mystic; John B. Routien, Lyme; Paul C. Watts, Mystic, all of Conn.; Riichiro Shibakawa, Handa; Junsuke Tone, Chita, both of Japan

[73] Assignee: Pfizer Inc., New York, N.Y.

[21] Appl. No.: 802,499

[22] Filed: Jun. 1, 1977

[51] Int. Cl.² ............................................. A61K 35/74
[52] U.S. Cl. .................................. 424/117; 195/80 R
[58] Field of Search ....................... 424/117; 195/80 R

[56] References Cited

U.S. PATENT DOCUMENTS 3,857,936  12/1974  Avgoudelis .......................... 424/117
4,031,206   6/1971  Celmer et al. ....................... 424/117

Primary Examiner—Jerome D. Goldberg
Attorney, Agent, or Firm—Connolly and Hutz

[57] ABSTRACT

A new sulfur-containing polypeptide antibiotic produced by two strains of Streptosporangium under submerged fermentation conditions is useful for the treatment of microbial infections and in improving feed utilization efficiency in ruminants.

4 Claims, 1 Drawing Figure

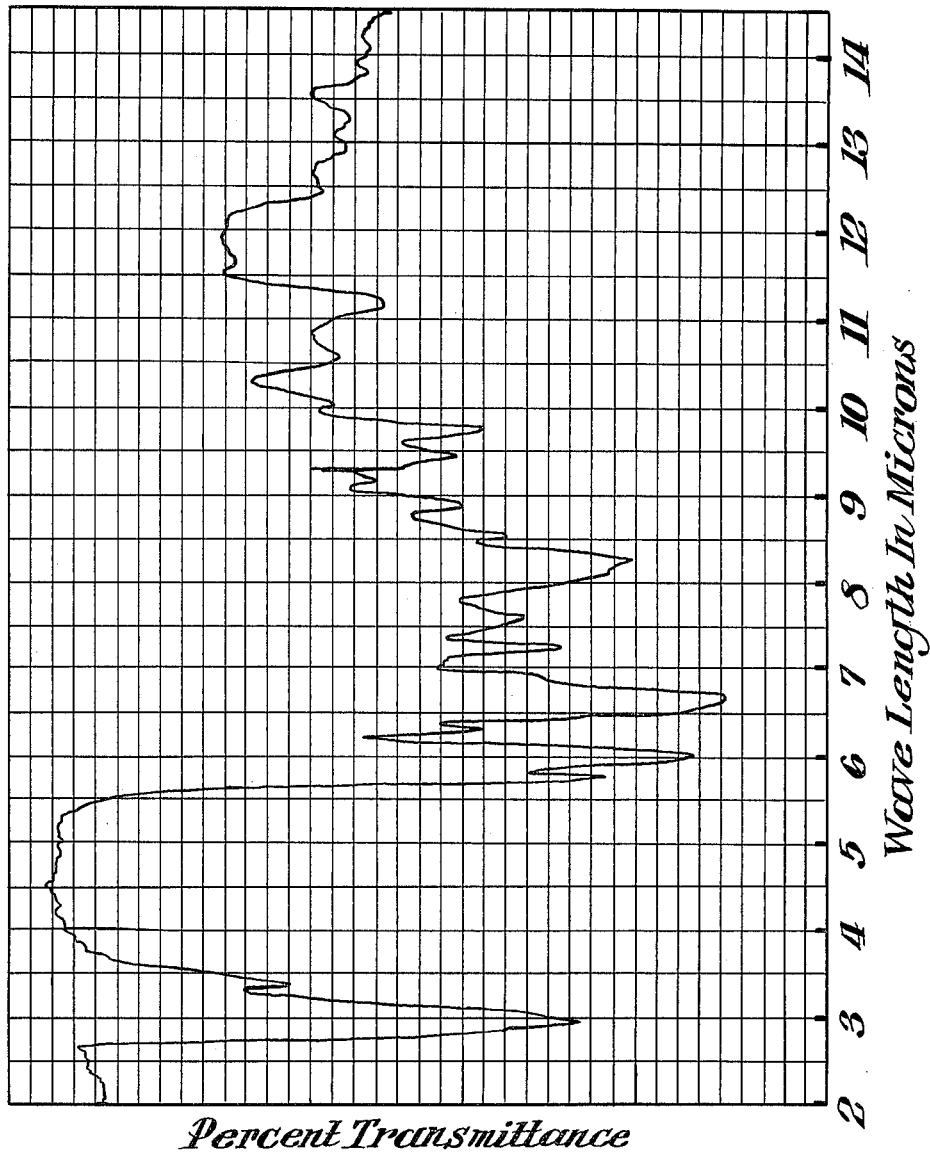

POLYPEPTIDE ANTIBIOTIC PRODUCED BY A NEW SUBSPECIES OF STREPTOSPORANGIUM

BACKGROUND OF THE INVENTION

This invention is concerned with a new member of the sulfur-containing polypeptide group of antibiotics. This family of antibiotics includes thiostrepton (Antibiotics Ann., 1955–1956, 554–559); siomycin (J. Antibiotics, 14:255, 1961); A-59 (J. Antibiotics, A14:194, 1961); thiopeptin (J. Antibiotics, 23:113–119, 1970); and sporangiomycin (J. Antibiotics, 21:525–531, 1968).

SUMMARY OF THE INVENTION

This invention is concerned with a new sulfur-containing polypeptide antibiotic produced by each of two strains of a new subspecies of Streptosporangium under submerged aerobic conditions in aqueous nutrient media. The antibiotic Compound 46,192 is active against a variety of microorganisms and acts to improve feed efficiency in ruminants.

DETAILED DESCRIPTION OF THE INVENTION

The antibiotic producing microorganisms of the present invention, isolated from soil samples in Canada and France, were found on examination to have the morphological features of a Streptosporangium. This genus is differentiated from others belonging to the group of actinomycetes by the production of coiled chains of round to elliptical spores contained in sporangia and the production of aerial mycelium on the surface of the culture.

The two strains of Streptosporangium, Pfizer F. D. 25824 and Pfizer F. D. 25898, have been deposited in The American Type Culture Collection, Rockville, Md. under their accession numbers ATCC 31265 and ATCC 31266, respectively. The permanency of the deposit and ready accessibility thereto by the public are afforded in the event the patent is granted. Access to the cultures is available during pendency of the application under Rule 14 and 35 USC 112. All restrictions on the availability to the public of the cultures deposited will be irrevocably removed upon granting of the patent.

Both cultures were prepared for planting on media by the method described in *Inter. Jr. Sys. Bacteriology* 16(3):322, 1966. The incubation temperature was 28° C. Readings of results were made at intervals up to 21 days. The colors of the cultures were made by comparison with chips from the Color Harmony Manual, fourth edition, as well as personal descriptive terms.

Identification media used for the characterization of the cultures and references for their composition are as follows:

1. Tryptone — Yeast Extract Broth (ISP#1 — Difco)
2. Yeast Extract Malt Extract Agar (ISP#2 — Difco)
3. Oatmeal Agar (ISP#3 — Difco)
4. Inorganic Salts — Starch Agar (ISP#4 — Difco)
5. Glycerol — Asparagine Agar (ISP#5 — Difco)
6. Peptone-Yeast Extract Iron Agar (ISP #6 — Difco)
7. Tyrosine Agar (ISP#7 — Difco)
8. Dextrose-Nitrate Broth — S. A. Waksman, *The Actinomycetes*, Vol. 2, medium 1, page 328, 1961, with 3 g dextrose substituted for 30 g sucrose and agar omitted.
9. Organic Nitrate Broth — R. E. Gordon and J. M. Mihm. Jr. Bac. 73: 15–27, 1957.
10. Gelatin — Ibid.
11. Starch — Ibid.
12. Skim Milk — Difco.
13. Tap Water Agar
14. Glucose Asparagine Agar — S. A. Waksman, op. cit. medium 2, p. 328.
15. Czapek Sucrose Agar — Ibid, medium 1, p. 328.
16. Emerson's Agar — Ibid, medium 28, p. 331.
17. Nutrient Agar — Ibid, medium 14, p. 330.
18. Calcium Malate Agar — S. A. Waksman, Bact. Rev. 21:1–29, 1957.
19. Cellulose
    a. H. L. Jensen, Proc. Linnean Soc. N. S. Wales 55:231–248, 1930.
    b. M. Levine and H. W. Schoelein, A Compilation of Culture Media, medium 2511, 1930.
20. Carbohydrates — G. M. Luedemann and B. C. Brodsky, Antimicrobial Agents and Chemotherapy 1964: 47, 1965.

The cultures were characterized as follows:

Yeast-Malt Extract Agar — Growth moderate to good, raised, colorless to pinkish red (6½ gc and 6½ le) with white aerial mycelium that becomes pink in 21 days; reverse white to pinkish; pale pink soluble pigment in 21 days.

Oatmeal Agar — Growth poor to moderate, cream colored to pale pinkish (6 ca), appearing as small isolated colonies with velvety surface, aerial mycelium continuous throughout or ring-like; reverse cream-colored to pale pinkish; pale pinkish soluble pigment.

Inorganic Salts — Starch Agar — Growth poor to moderate, pale pink or colorless (5 ca to 6 ca), aerial mycelium ring-like; reverse like surface; no soluble pigment.

Glycerol Asparagine Agar — Growth poor, small isolated dots, white; reverse colorless to cream colored; no soluble pigment.

Czapek Sucrose Agar — Growth poor, pale pinkish (6 ca) to white, small isolated dots; reverse white; no soluble pigment.

Gluclose Asparagine Agar — Growth poor to moderate, white, slightly raised, smooth with little aerial mycelium; reverse the color of the surface; no soluble pigment.

Nutrient Agar — Growth poor to moderate, pale yellowish, raised, slightly wrinkled, with a little white or no aerial mycelium; reverse same color as surface; no soluble pigment.

Emerson's Agar — Growth moderate, pale yellowish, highly raised, wrinkled, no aerial mycelium or small areas of white aerial mycelium; reverse like surface in color; no soluble pigment.

Starch Agar — Growth moderate to good, white to pale grayish, raised, wrinkled, no aerial mycelium; reverse brownish (4 le); pale pinkish soluble pigment.

Gelatin — Growth moderate, white, slightly raised, wrinkled; reverse yellowish brown (3 ic); very pale pinkish to no soluble pigment.

Calcium Malate Agar — Growth poor, white to pale pinkish (near 6 ca) appearing as small isolated dots; reverse colorless; no soluble pigment.

Tyrosine Agar — Growth poor to moderate, white to pale pink, appearing as small isolated dots; pinkish soluble pigment.

Tap Water Agar — White to pale pink small dots; reverse the same color as surface, no soluble pigment.

Sporangia and spores (from Czapek Sucrose Agar) — sporangia mostly round, 6.5-10 (most 7-8) μ wide on sporangiophores 13-14 μ long; spores round to broadly elliptical, mostly 2.2 × 1.6 μ but varying from 1.6-2.7 × 1.1-2.2 μ or round, 2.2 μ wide; non-motile.

Biochemical Properties — No melanin produced; no $H_2S$; gelatin liquefied; starch very weakly hydrolyzed; nitrates reduced; growth on Jensen's cellulose but no disintegration and no growth on Levine and Schoelein's cellulose; no action on milk; calcium malate not hydrolyzed.

Carbon utilization — Utilized: glucose, cellobiose, fructose, galactose, inositol, mannose, rhamnose, ribose, starch, trehalose, xylose; not utilized: adonitol, arabinose, dulcitol, glycerol, lactose, mannitol, melezitose, raffinose, sorbitol, sorbose, sucrose; variable for the two strains: melibiose, salicin.

The two cultures were also grown on a few media as outlined by J. N. Couch, Jr. Elisha Mitchell Soc. 79:53-70 1963 and also tested for growth at different temperatures on ATCC medium #172. Results follow:

Czapek-Sucrose Agar — Colonies 8-11 mm. wide in 4-5 weeks, flat, thin, with fimbriate radial lines of pink aerial mycelium at edge or with halo of suppressed pale pink mycelium; aerial mycelium Hydrangea Pink to Pale Congo Pink (Ridgway).

Peptone Czapek Agar — Colonies 10-15 mm. wide, flat to slightly raised, slightly roughed in central portion but with flat outer part, margin regular, mostly naked, Olive Buff to Pale Olive Buff (Ridgway), some white aerial mycelium near edge; soluble pigment very pale pinkish to pinkish-vinaceous.

Potato Dextrose Agar — Colonies 10-15 mm. wide, raised, somewhat roughened, covered with whitish to pink aerial mycelium (Pale Congo Pink — Ridgway), edge entire; tan soluble pigment.

Emerson's Agar — Colonies 12-17 mm. wide; raised noticeably, irregularly roughened over entire surface, edge irregular, naked, color near Deep Olive Buff (Ridgway).

Temperature Relations

| 42° C | 37° | 28° | 21° |
| --- | --- | --- | --- |
| No growth | Good Growth | Good Growth | Good Growth |

The two new cultures of Streptosporangium were compared with closely related *Streptosporangium roseum* ATCC 12428 and *S. vulgare* subsp. antibioticum ATCC 21906. The two new cultures were found to be different from *S. vulgare* subsp. antibioticum ATCC 21906 but similar to *S. roseum* ATCC 12428 in many aspects. On ISP Medium 2, ISP Medium 3, ISP medium 5, tyrosine agar, Czapek-sucrose agar, Czapek-peptone agar, Emerson's agar, nutrient agar, tap water agar, potato carrot agar and calcium malate agar, the colonies of the two new cultures closely resembled those of *S. roseum*. The two new cultures and *S. roseum* showed positive starch hydrolysis, positive gelatin liquefaction, positive nitrate reduction, negative melanin production, negative cellulose disintegration and the same range of growth temperature. The size and shape of sporangia and sporangiospores of the three cultures were identical. The pattern of utilization of seven carbohydrates was similar among the three cultures.

Compared with those of *S. roseum*, colonies of the two new cultures were different on potato dextrose agar and starch agar and were slightly different on ISP Medium 4, glucose-asparagine agar and gelatin agar. *Streptosporangium roseum* utilized arabinose whereas the two new cultures did not.

It was concluded, based on cultural, morphological and comparison data, that the two new cultures are indistinguishable from each other and represent a new subspecies of *Streptosporangium roseum*. Because of their pink color, the name proposed for the two new cultures is *Streptosporangium roseum* subsp. incarnatum Routien subsp. nov.

Cultivation of the Streptosporangium cultures preferably takes place in nutrient media at a temperature of 28°-36° C., and under submerged aerobic conditions with agitation. Nutrient media which are useful for such purposes include a source of assimilable carbon such as sugars and starch; a source of organic nitrogen such as casein, enzymatic digest of casein, soybean meal, cottonseed meal, peanut meal and wheat gluten. A source of growth substances such as distillers' solubles, fish meal and yeast extract as well as salts such as sodium chloride and calcium carbonate and trace minerals such as iron, magnesium, zinc, cobalt and manganese may also be utilized with advantageous results. If excessive foaming is encountered during fermentation, anti-foam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of antibiotic Compound 46,192 may be obtained by employing growth from a slant of the culture on a medium such as ATCC Medium 172 (ATCC Catalogue, 10th edition, p. 235, 1972). The growth may be used to inoculate either shake flasks or inoculum tanks, or alternatively, the inoculum tanks may be seeded from the shake flasks. Growth in shaken flasks will generally have reached its maximum in about 4 days whereas inoculum in sugmerged inoculum tanks will usually be at the most favorable period in 2 to 3 days. Substantial antibiotic activity is obtained in the final fermentor stage in approximately 72 to 120 hours.

The process of antibiotic production is conveniently followed during fermentation by biological assay of the broth employing a sensitive strain of *Staphylococcus aureus*. Standard plate assay technique is employed in which the zone of inhibition surrounding a filter paper disc saturated with the broth is used as a measure of antibiotic potency. After the fermentation broth has reached a desired level of antibiotic potency, the antibiotic is isolated from either whole broth or filtered broth. In the latter case, the mycelium is removed by filtration or centrifugation. Various types of equipment such as filter presses, centrifuges, etc. may be employed.

Thin-layer chromatography employing silica gel is a useful tool for analyzing antibiotic Compound 46,192 co-produced with a number of minor antibiotic components in fermentation media and the composition of crude and purified materials extracted from fermentation broths. The resolution of the components of the antibiotic mixture is importantly dependent on antibiotic loading of the system. Too little antibiotic potency fails to reveal minor antibiotic components; too much antibiotic potency results in a dragging effect with resulting poor resolution.

The developing system for the thin-layer chromatography is $CHCl_3$: $(CH_3)_2CO$ (3:1 v/v). The antibiotics may be visualized by exposure to 254 mm light, spraying with water to detect water repellant spots or by overlaying with agar seeded with a sensitive strain of *Staphylococcus aureus*.

The components of the antibiotic mixture may be separated and recovered from fermentation broth by solvent extraction, counter-current distribution, adsorption, column chromatography or combinations thereof. The antibiotics may be extracted from whole broth at a pH range of 4.0 to 10.0 employing an organic solvent such as butanol, pentanol, ethyl acetate, methylisobutyl ketone and other related water-immiscible solvents. The solvent is then concentrated under vacuum and the antibiotics precipitated by the addition of a solvent such as n-heptane.

A method of separation and recovery of antibiotic Compound 46,192 is as follows: Whole fermentation broth adjusted to pH ca. 5.0 with 50% sulfuric acid is extracted with methylisobutyl ketone. The solvent is removed in vacuo. The dark oily concentrate is triturated with heptane, diethyl ether and finally with ethyl acetate. The resultant solid is then dissolved in methanol and precipitated by cooling to yield an off-white powder. A portion of this powder dissolved in chloroform is chromatographed on silica gel, preferably silica gel 60 (E. Merck, Darmstadt, Germany) and eluted with chloroform containing increasing amounts of methanol up to a maximum of 3% methanol-97% chloroform. Those fractions from column chromatography rich in Compound 46,192 are further purified by preparative thin-layer chromatography (silica gel $PF_{254}$-E. Merck, Darmstadt, Germany) developed and eluted with ethyl acetate. Compound 46,192 crystallizes from methanol. All steps in the purification sequence are monitored by thin-layer chromatography (Analtech silica gel GF, chloroform-acetone, 3:1). Compound 46,192 is visualized by (a) exposure to 254 nm ultraviolet light, (b) bio-overlay using an agar suspension containing a sensitive strain of *Staphylococcus aureus* or (c) water spray to detect water repellant spots.

Compound 46,192 is active against a variety of Gram-positive bacteria as illustrated in Table I.

Table I

| Organism | Minimum Inhibitory Concentration (mcg/ml) |
| --- | --- |
| *Staphylococcus aureus* sp. | < 0.10 |
| *Bacillus subtilis* | < 0.10 |
| *Streptococcus pyogenes* | < 0.10 |
| *Streptococcus faecalis* | < 0.10 |
| *Clostridium* sp. | < 0.12–3.12 |

Significant protection is afforded to mice experimentally infected with *Staphylococcus aureus* 01A005 by Compound 46,192 at doses of 50 to 200 mg/kg and an oral dose of 200 mg/kg.

Crude antibiotic mixtures such as those obtained directly from broth or in any of the intermediate recovery stages as well as purified Compound 46,192 may be employed in the treatment of antibiotic-sensitive infections in man and animals at parenteral doses of 200 to 1000 mg., depending on the type and severity of the infection and weight of the subject being treated. Solutions of Compound 46,192 in sesame oil, peanut oil and/or propylene glycol at concentrations of 200 to 500 mg/ml may be employed for subcutaneous or intramuscular administration.

The effect of growth promotants in animal feeds generally has been determined by direct animal feeding. British patent specification No. 1,197,826 details an in vitro technique for assessing potential growth promotant activity in ruminants. The test method involves the use of an apparatus in which the digestive processes of the ruminants are conducted and studies in vitro. The animal feeds, rumen inoculum and various growth promotants are introduced into and withdrawn from a laboratory unit under carefully controlled conditions and the changes taking place are studied critically and progressively during the consumption of the feed by the microbial flora in the rumen contents. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml added to a 50 ml conical flask containing 400 mg of standard substrate (68% corn starch + 17% celluose + 15% extracted soybean meal), 10 ml of a pH 6.8 buffer and the test compound. The flasks are gassed with oxygen free nitrogen for about 2 minutes and incubated in a shaking water bath at 39° C. for about 16 hours. All tests are conducted in triplicate.

After incubation, 5 ml of the sample are mixed with 1 ml of 25% metaphosphoric acid. After 10 minutes, 0.25 ml of formic acid is added and the mixture centrifuged at 1500 r.p.m. for 10 minutes. Samples are then analyzed by gas-liquid chromatography by the method of D. W. Kellog in J. Dairy Science 52, 1690 (1969). Peak heights for acetic, propionic and butyric acids are determined for samples from untreated and treated incubation flasks. Results are shown in Table II.

Table II

| Compound | Concentration (ppm) | Propionic acid (%)* |
| --- | --- | --- |
| 46,192 | 20 | 165 |
|  | 10 | 159 |
|  | 5 | 163 |

*Untreated control = 100%.

Based on these data, it can be projected that improvement of feed utilization by ruminants such as cattle and sheep and monogastric animals such as horses, pigs and rabbits will be obtained with the incorporation of Compound 46,192 in animal feeds. In addition to pure Compound 46,192 and the crude isolated compound, dried fermentation broth containing antibiotic Compound 46,192 may be incorporated in feed compositions at the desired potency concentration.

EXAMPLE I

A sterile aqueous medium having the following composition is prepared:

| Ingredient | Grams/liter |
|---|---|
| Glucose | 10 |
| Starch | 20 |
| Enzymatic digest of casein | 5 |
| Dipotassium hydrogen phosphate | 0.5 |
| Cobalt chloride | 0.002 |
| Calcium carbonate | 4 |
| Meat meal | 5 |
| Yeast extract | 5 |
| pH 7.1–7.2 | |

Cells from a slant of *S. roseum* subsp. incarnatum ATCC 31265 on ATCC medium 172 are transferred to a series of 300 ml flasks each containing 50 ml of this medium and shaken on a rotary shaker for 3–4 days at 28°–30° C. Aliquots of this grown inoculum are transferred to 300 ml flasks each containing 100 ml of the sterile medium shown above. After shaking for 3–4 days at 28°–30° C., 5–10% v/v of the grown inoculum is transferred to a 4 liter fermentor containing 2 liters of the following sterile medium:

| Ingredient | Grams/liter |
|---|---|
| Glucose | 20 |
| Soy flour | 30 |
| Corn steep liquor | 5 ml |
| Cobalt chloride | 0.002 |
| pH 6.9–7.1 | |

The fermentation is conducted for 70 to 120 hours at 30° C. with stirring at 1700 rpm and aeration at about one volume of air per volume of broth per minute. The whole broth is twice extracted with ½ volume of methylisobutyl ketone following adjustment of the pH to 5.0 with 50% acid. The combined solvent extracts are concentrated in vacuo and the antibiotic activity precipitated by the addition of several volumes of n-heptane. The solids are collected by filtration or centrifugation.

EXAMPLE II

The method of Example I may be repeated with comparable results employing *Streptosporangium roseum* subsp. incarnatum ATCC 31266 in place of *Streptosporangium roseum* subsp. incarnatum ATCC 31265 and a fermentation medium of the following composition:

| Ingredient | Grams/liter |
|---|---|
| Glucose | 10 |
| Starch | 20 |
| Yeast extract | 5 |
| Enzymatic digest of casein | 5 |
| Cobalt chloride | 0.002 |
| Calcium carbonate | 1 |
| pH 6.9–7.1 | |

The whole fermentation broth is taken to dryness, preferably by spray-drying.

EXAMPLE III

A large scale fermentation was conducted employing the inoculum and production media of Example I. A 50 gallon fermentor containing 25 gallons of the production medium of Example I, after being inoculated with a 5% v/v inoculum of *S. roseum* subsp. incarnatum 31265 was run for 5 days at 30° C. with an aeration rate of one volume of air per volume of broth per minute. Twenty five gallons of whole fermentation broth was extracted with 8 gallons of methylisobutyl ketone following its adjustment to pH 5 with 50% sulfuric acid. The solvent was removed in vacuo leaving a dark oil. This was triturated in turn with 250 ml of heptane, 50 ml of diethyl ether and then with 25 ml of ethyl acetate. The resultant solid was then dissolved in methanol and precipitated by cooling to yield 1.77 grams of an off-white powder. A portion of this powder (1.50 g) was dissolved in chloroform and chromatographed on a column containing approximately 230 g of silica gel 60 developed and eluted with chloroform containing increasing amounts of methanol up to a maximum of 3% methanol-97% chloroform. Those fractions from column chromatography rich in Compound 46,192 were further purified by preparative thin-layer chromatography employing silica gel $PF_{254}$. The material obtained by eluting with ethyl acetate was crystallized from methanol, m.p. 210°–216° C.

Compound 46,192 is soluble in chloroform, ethyl acetate and methylisobutyl ketone; partially soluble in methanol; and insoluble in heptane.

Exhaustive acid hydrolysis of Compound 46,192 indicates the presence of threonine and several unidentified amino acids. The $C^{13}$ NMR ($CDCl_3$) spectrum suggests the presence of some 73 carbon atoms.

Analysis gives the following average proportions:

| | |
|---|---|
| Carbon | 48.49 |
| Hydrogen | 5.05 |
| Nitrogen | 13.03 |
| Sulfur | 10.88 |
| Oxygen (by difference) | 22.55 |

Comound 46,192 is optically active having a rotation of $[\alpha]_D = -129°$ (c = 1.0, $CHCl_3$).

The ultraviolet absorption maxima in ethanol are as follows:

| max $\lambda$ | 238 . 300–305 $_{sh}$ nm | $E_{1cm}^{1\%}$ | 350 80 |
|---|---|---|---|

The infrared spectrum of Compound 46,192 is shown in FIG. 1. A potassium bromide pellet shows characteristic absorption in the infrared region at the following wavelengths in microns: 2.97, 5.77, 6.02, 6.30, 6.6 – 6.75, 7.25, 8.25, 9.75 and 11.20.

What is claimed is:

1. Antibiotic Compound 46,192 when in the crystalline form has a melting point of 210°–216° C., is soluble in chloroform, ethyl acetate, methylisobutyl ketone and insoluble in heptane; has absorption maxima in ethanol in the ultraviolet light region of the spectrum at 238 and 300–305$_{sh}$nm with $E_{1cm}^{1\%}$ values of 350 and 80, respectively; has the average composition by weight of 48.49% carbon, 5.05% hydrogen, 13.03% nitrogen, 10.88% sulfur and 22.55% oxygen (by difference); has an optical rotation of $[\alpha]_D = -129°$ at a concentration of 1% in chloroform; and when pelleted in KBr, exhibits characteristic absorption in the infrared region at the following wavelengths in microns: 2.97, 5.77, 6.02, 6.30, 6.6–6.75, 7.25, 8.25, 9.75 and 11.20.

2. Process for producing antibiotic compound 46,192 cultivating *Streptosporangium roseum* subsp. incarnatum Routien ATCC 31265 or *Streptosporangium roseum* subsp. incarnatum Routien ATCC 31266 under submerged aerobic conditions in an aqueous nutrient medium containing an assimilable source of carbon and nitrogen until substantial antibiotic activity is obtained and separating said antibiotic therefrom.

3. The method for the improvement of feed utilization by ruminants and monogastric animals which comprises orally administering to said animals antibiotic Compound 46,192 as defined in claim 1 at a level of 5 to 20 ppm.

4. The method of claim 3 wherein antibiotic Compound 46,192 is contained in the dried fermentation medium of claim 2.